United States Patent [19]

Chemerda et al.

[11] 4,048,224
[45] Sept. 13, 1977

[54] PROCESS FOR RESOLVING ALANINE, 3-FLUORO AND 2-DEUTERO-3-FLUORO-DL-ALANINE

[75] Inventors: John M. Chemerda; George Gal, both of Watchung, N.J.

[73] Assignee: Merck & Co., Inc., Rahway, N.J.

[21] Appl. No.: 664,328

[22] Filed: Mar. 5, 1976

[51] Int. Cl.$^2$ .................. C07C 101/10; A61K 31/195
[52] U.S. Cl. ............................... 260/534 C; 424/319
[58] Field of Search ..................................... 260/534 C

[56] References Cited

U.S. PATENT DOCUMENTS

| 3,028,395 | 4/1962 | Gillingham | 260/534 C |
| 3,381,031 | 4/1968 | Dwyer et al. | 260/534 C |

OTHER PUBLICATIONS

Dane et al., Agnew. Chem. Internat., Edit. 1, 658 (1962).
Poroshin et al., Chem. Abst., vol. 80, 48400; (1974).
Asai et al., Chem. Abst., vol. 80, 133825w (1974).
Rogozhin et al., Chem. Abst., vol. 82, 98436n (1975).

*Primary Examiner*—James O. Thomas, Jr.
*Assistant Examiner*—G. T. Breitenstein
*Attorney, Agent, or Firm*—Hesna J. Pfeiffer; Julian S. Levitt

[57] ABSTRACT

DL-Alanine, 3-fluoro-DL-alanine and 2-deutero-3-fluoro-DL-alanine, are resolved by reaction with a resolving base and a $\beta$-dicarbonyl compound. The resulting azomethine diastereomeric salts which are easily separated, the masking group is readily removed under mildly acidic conditions.

5 Claims, No Drawings

PROCESS FOR RESOLVING ALANINE, 3-FLUORO AND 2-DEUTERO-3-FLUORO-DL-ALANINE

In summary, this invention is concerned with the preparation of 3-fluoro-D-alanine and 2-deutero-3-fluoro-D-alanine which are potent antibacterial agents valuable in inhibiting the growth of pathogenic bacteria of both the gram-positive and gram-negative types. More particularly, it relates to the production of D-alanine 3-fluoro-D-alanine and 2-deutero-3-fluoro-D-alanine in substantially pure form by reaction of DL-alanine 3-fluoro-DL-alanine or 2-deutero-3-fluoro-DL-alanine with a resolving base such as quinine, quinidine, brucine, strychnine, d or 1-α,N,N-trimethylbenzylamine or the like and a β-dicarbonyl compound of the formula

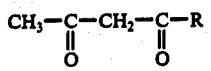

wherein R is methyl, phenyl, or alkoxy of 1-5 carbon atoms, especially ethoxy.

This resolution process, although only applied herein to alanine compounds, is of general applicability to all other α-amino acids.

This reaction is conducted using approximately equimolar amounts of the three reactants. A lower alkanol of 1-5 carbon atoms is used as a solvent, preferably methanol. The reaction takes place at reflux of the solvent, and the reaction time is from ½-3 hours.

The reaction mixture is then cooled to about room temperature, and allowed to age for a brief time, about 15 min. to 1 hour. The two diasteromeric salts are then easily separable. For instance, in the case of fluoroalanine and quinine, the L-isomer is recovered as a solid precipitate. The solid L-isomer is recovered by filtration. To increase the yield, the filtrate can be concentrated in vacuo to a syrup and then flushed with another solvent in which there is varying solubility between isomers in order to recover the second crop. A suitable solvent in the case of fluoroalanine is ethyl acetate. A volume excess of the solvent is added, and the mixture aged for up to 36 hours, if desired. Following this aging, the other isomer can be easily recovered by filtration.

The D-isomer is recovered from the solvent, the alkanol of the original reaction or the alkanol/ethyl acetate mixture, by concentrating the filtrate. The crude solid D-isomer is thereby obtained.

The new separated salt pairs of the two diastereomers can be treated identically to recover the optically active amino acid in pure form. First, the resolving base is separated from the isomer by mixing the crude isomer with aqueous alkali metal hydroxide, e.g., sodium hydroxide or potassium hydroxide. This reaction takes place practically instantaneously, but the solution can be aged for several minutes to 30 min. The base precipitates, and can be extracted using a solvent such as chloroform.

The aqueous solution is then acidified to pH 6 or less, using any easily available acid such as hydrochloric acid, acetic acid, formic acid, or mixtures thereof. The clear solution thereby obtained is then extracted using chloroform to remove the β-dicarbonyl compound. The resulting acidified solution is then purified by desalting using an ion exchange resin on H+ cycle, then eluated with dilute ammonium hydroxide.

The following examples illustrate this invention:

EXAMPLE 1

To a solution of 17.2 g quinine and 5.5 g. 2,4-pentanedione in 100 ml. of methanol is added 5.35 g. D,L-3-fluoroalanine. The mixture is refluxed in an inert atmosphere for 60 min. The resulting solution is cooled to 20°-22° C., aged for 1 hour, then the crystalline quinine salt of L-N-[1-methyl-2-acetylvinyl]-α-amino-β-fluoro propionic acid is filtered, washed with cold methanol and dried in vacuo. Weight: 9.9 g.

The filtrate is concentrated in vacuo and treated with 30 ml. of ethyl acetate. After keeping it at around 0° C. for several hours the solid was filtered, washed with EtOAc, dried in vacuo, weight 3.0 g.

The solids are combined and dissolved in 20 ml. water. To separate the quinine 26.5 ml. of 1N sodium hydroxide solution is added slowly with stirring. The mixture is extracted four times with chloroform (at 25 ml.). To the aqueous phase is added 15 ml. 2N acetic acid and 19 ml. of 1N hydrochloric acid. After 10 min. the cleaved 2,4-pentanedione is separated by extracting the aqueous solution with chloroform.

The acidic solution is passed through a Dowex 50 WX 4 (H+) column. The column is washed with distilled water until the eluate is no longer acidic. The L-3-fluoroalanine is eluted with 0.5N ammonium hydroxide. The total eluate is concentrated under good vacuum such that the solution temperature does not exceed 25° C. Concentration is continued until a slurry is obtained with volume of 10 ml. of less.

L-3-fluoroalanine is filtered, washed with small amount of cold water and dried in vacuo.

Yield = 1.4 g. (52.4%)
MP = 165°-167° C. (dec.)
$[\alpha]_D = +10.28°$ (c = 6 in 1N HCl)

The combined ethyl acetate filtrate and washes is concentrated in vacuo. The glassy residue is dissolved in 20 ml. of water and the D-3-fluoroalanine is isolated by the same method as described above.

Yield = 1.2 g. (45%) MP = 165°-167° C. (dec.)
$[\alpha]_D = 10.21°$ (c = 6% in 1N HCl)

EXAMPLE 2

To a solution of 3.24 g. quinine and 1.10 g. 2,4-pentanedione in 30 ml. of methanol is added 0.891 g. D,L-alanine. The mixture is heated under reflux until a solution is formed (90 min.). The methanol is removed in vacuo and the glass residue is recrystallized from 100 ml. ethyl acetate.

The yield of the quinine salt of N-[1-methyl-2-acetylvinyl]-L-α-aminopropionic acid is 2.3 g. (93%).

The L-alanine is liberated from this salt by the method described in Example 1.

Yield of L-alanine = 382 mg. (86%)
MP = 297° C. (dec.)
$[\alpha]_D^{22} = 8.6$ (conc = 6% in 1N HCl)

EXAMPLE 3

100 g. of 2-Deutero-3-fluoro-DL-alanine are treated as described in Example 1.

The following results were obtained:
2-Deutero-3-fluoro-D-alanine:
  1st crop; yield 57% $[\alpha]_D = -10.68°$
  2nd crop; yield 7.6% $[\alpha]_D = -10.30°$
2-Deutero-3-fluoro-L-alanine:
  1st crop; yield 68% $[\alpha]_D = +10.1°$
  2nd crop; yield 1.56% $[\alpha]_D = +4.87°$

What is claimed is:

1. The process for resolving a DL-mixture of an alanine compound which is alanine, 3-fluoroalanine, or 2-deutero-3-fluoro alanine which comprises reacting approximately equimolar amounts of the alanine compound, a resolving base which is quinine, quinidine, brucine, strychnine, d-α,N,N-trimethylbenzylamine, or 1-α,N,N-trimethylbenzylamine, and a β-dicarbonyl compound of the formula

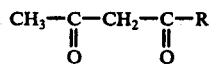

wherein R is methyl, phenyl or alkoxy of 1–5 carbon atoms, in a solution of a lower alkanol of 1–5 carbon atoms at reflux for ½–3 hours, and separating the salt parts of the diastereomers by crystallization, then treating both separately, first with an alkali metal hydroxide, then with $H_3O^+$, and recovering the respective individual isomers.

2. The process of claim 1 in which quinine is the resolving base.

3. The process of claim 1 in which R is methyl.

4. The process of claim 1 in which the alanine compound is DL-3-fluoroalanine.

5. The process of claim 1 in which the alanine compound is DL-2-deutero-β-fluoroalanine.